(12) United States Patent
Naidu

(10) Patent No.: US 9,637,501 B2
(45) Date of Patent: May 2, 2017

(54) PYRIDIN-3-YL ACETIC ACID MACROCYCLES AS INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventor: B. Narasimhulu Naidu, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/119,488

(22) PCT Filed: Feb. 19, 2015

(86) PCT No.: PCT/US2015/016493
§ 371 (c)(1),
(2) Date: Aug. 17, 2016

(87) PCT Pub. No.: WO2015/127003
PCT Pub. Date: Aug. 27, 2015

(65) Prior Publication Data
US 2017/0008908 A1    Jan. 12, 2017

Related U.S. Application Data

(60) Provisional application No. 61/942,244, filed on Feb. 20, 2014.

(51) Int. Cl.
*A61K 31/4545* (2006.01)
*C07D 401/04* (2006.01)
*C07D 498/18* (2006.01)

(52) U.S. Cl.
CPC ................... *C07D 498/18* (2013.01)

(58) Field of Classification Search
CPC ..................... A61K 31/4545; C07D 401/04
USPC .......................... 514/318; 546/194
See application file for complete search history.

(56) References Cited

U.S. PATENT DOCUMENTS 9,193,720 B2 * 11/2015 Naidu .................. C07D 417/14

FOREIGN PATENT DOCUMENTS

| WO | WO 2006/125178 A2 | 11/2006 |
| WO | WO 2010/130034 A1 | 11/2010 |
| WO | WO 2013/123148 A1 | 8/2013 |

* cited by examiner

*Primary Examiner* — Charanjit Aulakh
(74) *Attorney, Agent, or Firm* — Robert H. Brink; R. Steve Thomas; Edward R. Gimmi

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

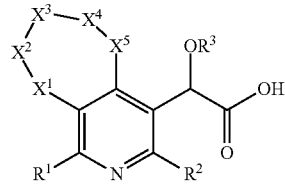

8 Claims, No Drawings

PYRIDIN-3-YL ACETIC ACID MACROCYCLES AS INHIBITORS OF HUMAN IMMUNODEFICIENCY VIRUS REPLICATION

CROSS-REFERENCE TO RELATED APPLICATIONS

This application is a 371 of International Application No. PCT/US2015/016493, filed 19 Feb. 2015, which claims priority of U.S. Provisional Application No. 61/942,244, filed 20 Feb. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2013123148, WO2014021867, WO20140028384, and WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I where:
$R^1$ is alkyl;
$R^2$ is alkyl;
$R^3$ is alkyl or haloalkyl;
$R^4$ is $(Ar^1)$alkyl or $Ar^1$;
$Ar^1$ is phenyl substituted with 0-3 substituents selected from halo, alkyl, haloalkyl, alkoxy, and haloalkoxy;
$X^1$ is phenyl;
$X^2$ is absent, O, $NR^4$, or $CH_2NR^4$;
$X^3$ is alkylene or alkenylene where the alkylene or alkeneyle can be substituted with 0-1 $Ar^1$ substituents;
$X^4$ is absent or O; and
$X^5$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, and haloalkoxy;
or a pharmaceutically acceptable salt thereof.

Another aspect of the invention is a compound of formula I where $R^3$ is alkyl; $R^4$ is $(Ar^1)$alkyl or $Ar^1$; $Ar^1$ is phenyl substituted with 0-3 substituents selected from halo, alkyl, haloalkyl, alkoxy, and haloalkoxy; $X^2$ is absent or $CH_2NR^4$; $X^3$ is alkylene or alkenylene where the alkylene or alkeneyle can be substituted with 0-1 $Ar^1$ substituents; $X^4$ is O; and $X^5$ is piperidinyl substituted with 0-3 alkyl substituents; or a pharmaceutically acceptable salt thereof.

Another aspect of the invention is a compound of formula I where $X^2$ is $CH_2NR^4$; $X^3$ is alkylene; and $X^4$ is O.

Another aspect of the invention is a compound of formula I where $X^2$ is O; $X^3$ is alkylene or alkenylene substituted with 1 $Ar^1$ substituents; and $X^4$ is O.

Another aspect of the invention is a compound of formula I where $X^5$ is piperidinyl substituted with 0-3 substituents selected from halo, alkyl, haloalkyl, alkoxy, and haloalkoxy.

For a compound of Formula I, the scope of any instance of a variable substituent, including $R^1$, $R^2$, $R^3$, $R^4$, $Ar^1$, $X^1$, $X^2$, $X^3$, $X^4$, and $X^5$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Cycloalkenyl" means a monocyclic ring system composed of 4 to 7 carbons. "Halo" means fluoro, chloro, bromo, or iodo. "Haloalkyl" and "haloalkoxy" include all halogenated isomers from monohalo to perhalo. "Aryl" includes carbocyclic and heterocyclic aromatic substituents. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}\ \mu M$ |
|---|---|
| 1 | 0.087 |
| 2 | 0.249 |
| 3 | 0.854 |
| 4 | 0.349 |
| 5 | 0.466 |
| 6 | 0.496 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "DCM" for dichloromethane, "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "prep-" for preparative, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compounds I-1 and I-6 are commercially available or synthesized by reactions well known in the art. Treatment of compounds I-1 with bromine provided the dibromo intermediates I-2 which was converted to the chloropyridines I-3 by reacting with POCl$_3$. Intermediates I-3 conveniently transformed to ketoesters I-5 using conditions well-known to those skilled in the art, including reacting I-3 with Grignard reagents in the presence of catalytic copper(I) bromide dimethylsulfide complex followed by alkyl 2-chloro-2-oxoacetate. Coupling of amines I-6 with intermediates I-5 in the presence of an organic base such as Hunig's base provided intermediate I-7. Chiral Lewis acid such as I-8 mediated reduction of ketoesters I-7 with catecholborane furnished chiral alcohols I-9. Tertiary butylation of alcohols I-9 using well-known conditions, including but not limited to tertiary-butyl acetate and perchloric acid, gave intermediates I-10. Intermediates I-10 are conveniently transformed to intermediates I-12 by using conditions well-known in the art, including but not limited to the Suzuki coupling between intermediates I-10 and I-11. The boronate or boronic acid coupling reagents, well-known in the art, are commercially available or are prepared by reactions well-known to those skilled in the art. Aldehydes I-12 are coupled to amines I-13 under reductive alkylation conditions such as NaCNBH$_3$/ZnCl$_2$ to provide intermediates I-14. Treatment of intermediates I-14 to ring closing metathesis conditions in the presence of Hoveyda-Grubbs catalyst provided the macrocycles I-15. Hydrolysis of intermediates I-15 by using conditions well-known to those skilled in the art furnished carboxylic acids I-16 which upon hydrogenation gave compounds I-17.

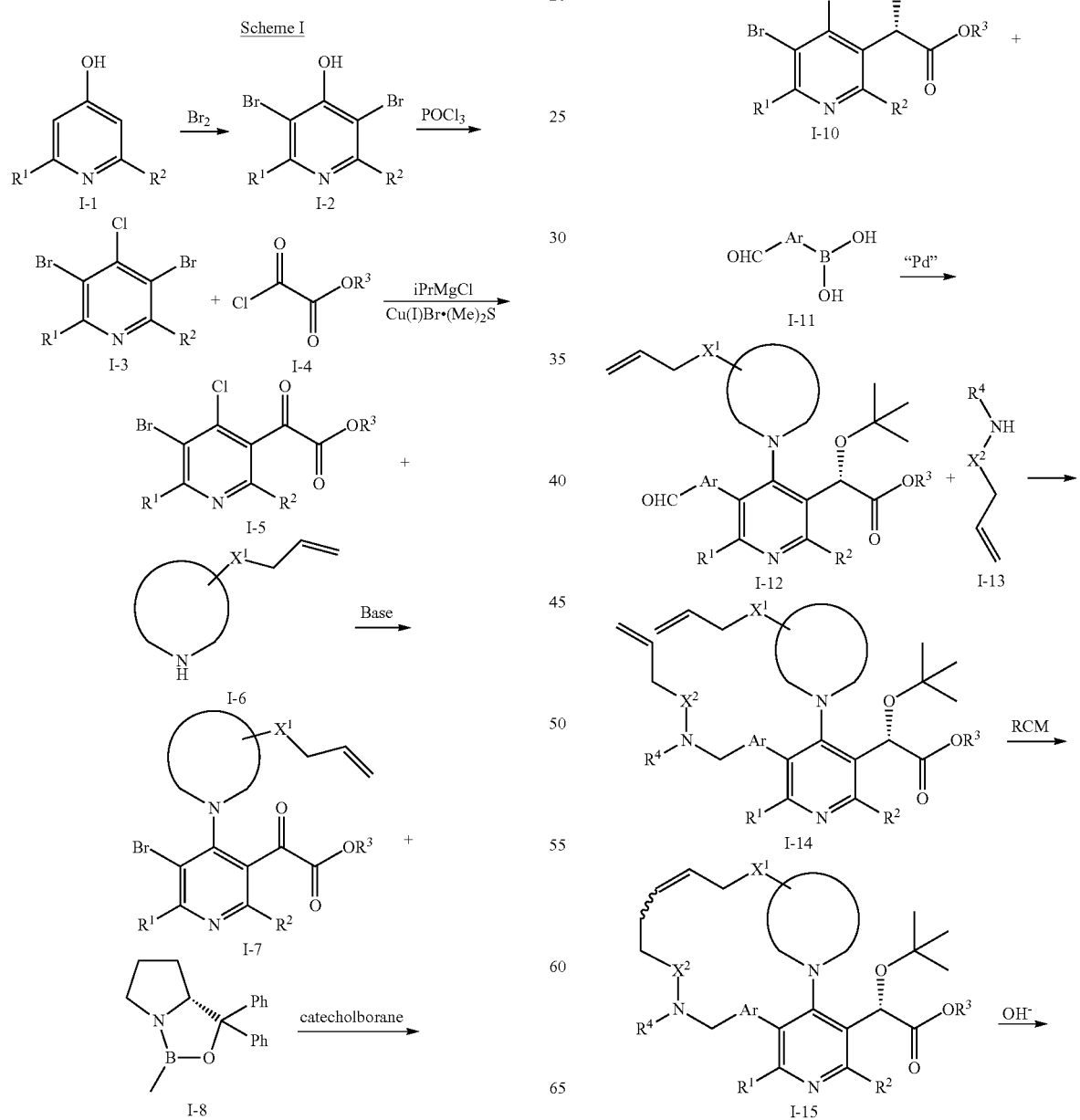

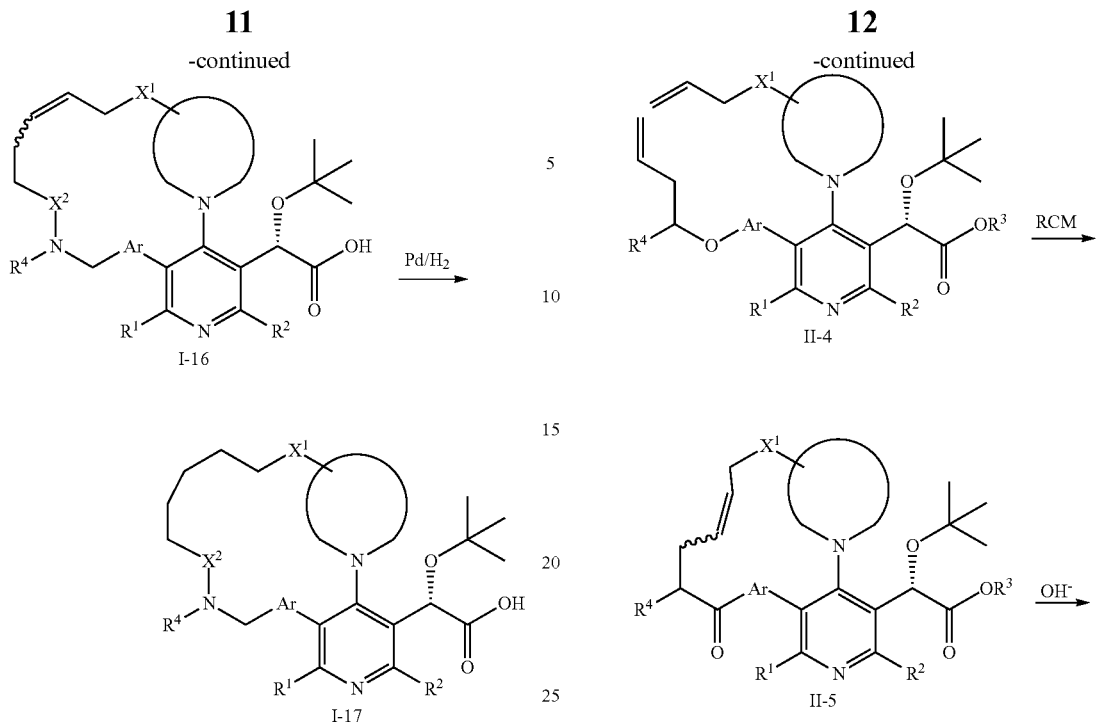

Some compounds of this invention can be prepared by the methods outlined in the Scheme II.

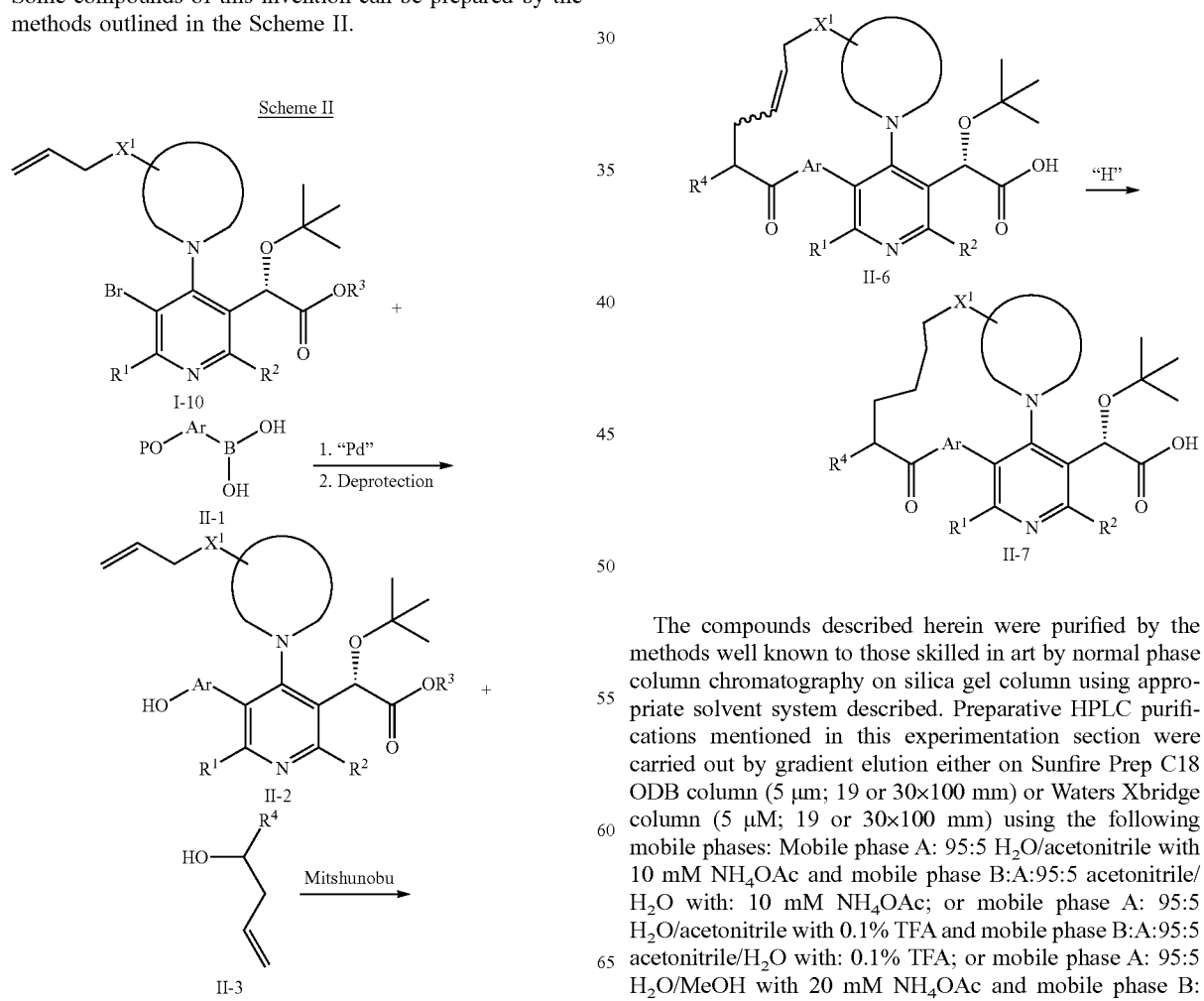

The compounds described herein were purified by the methods well known to those skilled in art by normal phase column chromatography on silica gel column using appropriate solvent system described. Preparative HPLC purifications mentioned in this experimentation section were carried out by gradient elution either on Sunfire Prep C18 ODB column (5 μm; 19 or 30×100 mm) or Waters Xbridge column (5 μM; 19 or 30×100 mm) using the following mobile phases: Mobile phase A: 95:5 $H_2O$/acetonitrile with 10 mM $NH_4OAc$ and mobile phase B:A:95:5 acetonitrile/$H_2O$ with: 10 mM $NH_4OAc$; or mobile phase A: 95:5 $H_2O$/acetonitrile with 0.1% TFA and mobile phase B:A:95:5 acetonitrile/$H_2O$ with: 0.1% TFA; or mobile phase A: 95:5 $H_2O$/MeOH with 20 mM $NH_4OAc$ and mobile phase B: 95:5 MeOH/$H_2O$ with 20 mM $NH_4OAc$.

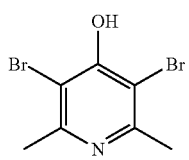

3,5-Dibromo-2,6-dimethylpyridin-4-ol, hydrobromide

A 3-neck R.B-flask equipped with mechanical stirrer, addition funnel and condesor is charged with 2,6-dimethylpyridin-4-ol (100 g, 812 mmol), $CH_2Cl_2$ (1000 mL) and MeOH (120 mL). To the resulting light brown or tan solution was added tert-BuNH2 (176 ml, 1665 mmol), cooled in water bath maintained between 5-10° C. (ice-water) and added dropwise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-$d_6$) δ 12.08 (br. s., 1H), 2.41 (s, 6H). LCMS (M+H)=281.9.

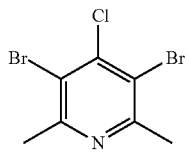

3,5-Dibromo-4-chloro-2,6-dimethylpyridine

A 500-mL rB-flask was charged with solid 3,5-dibromo-2,6-dimethylpyridin-4-ol, hydrobromide (22.2 g, 61.4 mmol) and $POCl_3$ (65 mL, 695 mmol) was added. To this white slurry was added N,N-dimethylaniline (15 mL, 118 mmol) and the reaction mixture was stirred at 130° C. (oil bath temp) for 1.5 h. Then, cooled, concentrated and the brown residue taken up in toluene (100 mL) and concentrated to remove any unreacted $POCl_3$. The residue was treated with ice (250 g) for 30 min and carefully neutralized with powder $Na_2CO_3$, extracted with ether (3×200 mL). The combined organic layers dried ($MgSO_4$/C), filtered, concentrated to give white slurry which was triturated with cold hexanes and filtered to afford 3,5-dibromo-4-chloro-2,6-dimethylpyridine (15.159 g, 50.6 mmol, 83% yield, contaminated with about 8 mol % dimethylaniline) as white solid. The filtrate was concentrated and purified by flash chromatography using 1-lit each hexanes. 1, 2, and 3% EtOAc/Hex to afford additional 3,5-dibromo-4-chloro-2,6-dimethylpyridine (4.888 g, 16.33 mmol, 26.6% yield) as white solid. $^1$H NMR (500 MHz, CDCl$_3$) δ 2.69 (s, 6H). LCMS (M+H)=300.0.

Alternative Procedure

A 1000-mL RB-flask was charged with solid 3,5-dibromo-2,6-dimethylpyridin-4-ol, hydrobromide (67 g, 185 mmol) and chloroform (70 ml). To this white slurry was added TEA (19 ml, 136 mmol) and POCl3 (50 ml, 536 mmol). The reaction mixture was refluxed for 1 h, added another portion of TEA (19 ml, 136 mmol), refluxed for 0.5 h and added TEA (19 ml, 136 mmol). The reaction mixture was stirred for 1 h. The reaction mixture was cooled down, concentrated to dryness. Ttoluene (100 mL) was added to the brown residue and concentrated to remove any unreacted $POCl_3$. Then, the residue was treated with ice (250 g) for 30 min and carefully neutralized with powder $Na_2CO_3$, extracted with $CH_2Cl_2$ (3×250 mL). The combined org layers was washed with aq. NaOH (3×, 1N), brine, dried ($MgSO_4$), filtered, concentrated to give beige solid which was treated with ether (200 mL), filtered, washed the solid with ether (2×30 ml) to afford a beige solid. The mother liquor was further purified by flash column chromatography (EtOAc/hexanes: 0 to 5%) to afford another crop of the product. The total of the product was 9.9 g (70%).

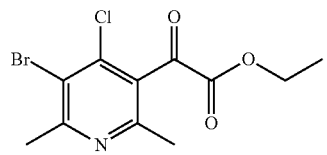 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate

To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added dropwise 2M iPrMgCl/THF (26.2 ml, 52.4 mmol) at −60° C. over 5 min. Then, the resulting slurry was warmed to −15° C. over 30 min and stirred for 30 min. The homogeneous brown reaction mixture was rapidly transferred via cannula to a solution of ethyl 2-chloro-2-oxoacetate (6.14 ml, 54.9 mmol) in THF (50 mL) maintained at −50° C. The resulting reaction mixture was stirred (1.5 h) while warming to 0° C. Then, taken up in to $Et_2O$ (200 mL), washed with 1:1 sat $Na_2CO_3$/1M $NH_4Cl$ (3×50 mL), dried ($MgSO_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)=322.1.

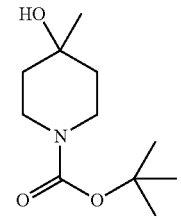

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO$_4$, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. $^1$H NMR (400 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

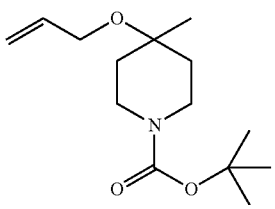 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

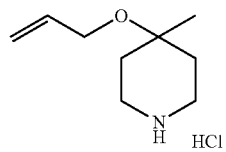

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, CD$_3$OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Free base (brown solid) is obtained by stirring HCl salt with aq Na$_2$CO$_3$ and extracting with DCM.

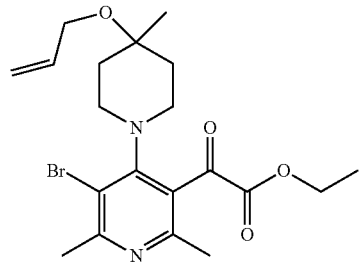 [SMILES: C=CCOC1(C)CCN(c2c(Br)c(C)nc(C)c2C(=O)C(=O)OCC)CC1]

Ethyl 2-(4-(4-(allyloxy)-4-methylpiperidin-1-yl)-5-bromo-2,6-dimethylpyridin-3-yl)-2-oxoacetate To a solution of 4-(allyloxy)-4-methylpiperidine (1.322 g, 8.52 mmol) and DIEA (1.487 ml, 8.52 mmol) in anhydrous toluene (10 mL) was added ethyl 2-(5-bromo-4-chloro-2,6-dimethylpyridin-3-yl)-2-oxoacetate (0.91 g, 2.84 mmol) at rt. The resulting mixture was placed in a pre-heated oil bath (90° C.). After 48 h, diluted with EtOAc (50 mL), washed with 1M HCl (10 mL), water (20 mL) and brine (10 mL). The combined aq layers extracted with EtOAc (2×25 mL) and the combined org layers dried (MgSO$_4$), filtered and concentrated to give yellow residue which was purified by flash chromatography using 5, 10 and 20% EtOAc, EtOAc and 20% MeOH/EtOAc to afford ethyl 2-(4-(4-(allyloxy)-4-methylpiperidin-1-yl)-5-bromo-2,6-dimethylpyridin-3-yl)-2-oxoacetate (0.6657 g, 1.515 mmol, 53.4% yield), yellow paste. LCMS (M+H)=441.4.

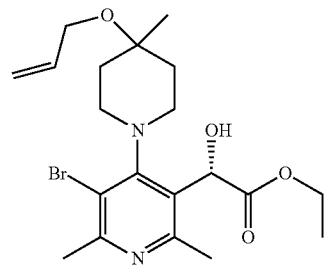 [SMILES: C=CCOC1(C)CCN(c2c(Br)c(C)nc(C)c2[C@H](O)C(=O)OCC)CC1]

(S)-Ethyl 2-(4-(4-(allyloxy)-4-methylpiperidin-1-yl)-5-bromo-2,6-dimethylpyridin-3-yl)-2-hydroxyacetate A mixture of ethyl 2-(4-(4-(allyloxy)-4-methylpiperidin-1-yl)-5-bromo-2,6-dimethylpyridin-3-yl)-2-oxoacetate (2.22 g, 5.05 mmol) and (R)-1-methyl-3,3-diphenylhexahydropyrrolo[1,2-c][1,3,2]oxazaborole (0.280 g, 1.011 mmol) in anhydrous toluene (25 mL) was warmed until the reaction mixture turns homogeneous solution. Then, cooled to −35° C. and 50% catecholborane/toluene (1.623 ml, 7.58 mmol) was added dropwise over 30 min. The reaction mixture was slowly warmed to −20° C. over 1 h and left in the freezer maintained at −15° C. for 43 h. Then, diluted with EtOAc (100 mL) and vigorously stirred with sat Na$_2$CO$_3$ (25 mL) for 30 min. Aqueous layer separated and organic layer washed with sat Na$_2$CO$_3$ (5×25 mL) by vigorously stirring for 15 each time, then dried (MgSO$_4$), filtered and concentrated to give crude as pale yellow paste which was purified by flash chromatography using 10, 20, 30 and 40% EtOAc/Hex to afford (S)-ethyl 2-(4-(4-(allyloxy)-4-methylpiperidin-1-yl)-5-bromo-2,6-dimethylpyridin-3-yl)-2-hydroxyacetate (1.8925 g, 4.29 mmol, 85% yield). LCMS (M+H)=443.3.

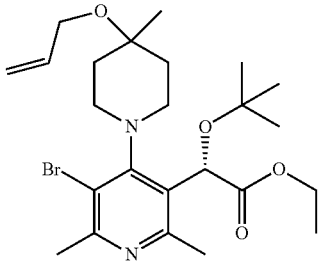 [SMILES: C=CCOC1(C)CCN(c2c(Br)c(C)nc(C)c2[C@H](OC(C)(C)C)C(=O)OCC)CC1]

(S)-Ethyl 2-(4-(4-(allyloxy)-4-methylpiperidin-1-yl)-5-bromo-2,6-dimethylpyridin-3-yl)-2-(tert-butoxy)acetate To a stirred solution of (S)-ethyl 2-(4-(4-(allyloxy)-4-methylpiperidin-1-yl)-5-bromo-2,6-dimethylpyridin-3-yl)-2-hydroxyacetate (1.89 g, 4.28 mmol) and tert-BuOAc (100 mL, 740 mmol) and CH$_2$Cl$_2$ (30 mL) was added 70% HClO$_4$ (1.104 ml, 12.85 mmol) and sealed with septa. After 2.5 h, the reaction mixture was quenched by careful addition of sat Na$_2$CO$_3$, organic layer separated, dried (MgSO$_4$), filtered, concentrated and purified by flash chromatography using 5, 10, 20, 30, 40 and 50% EtOAc/Hex to afford desired (S)-ethyl 2-(4-(4-(allyloxy)-4-methylpiperidin-1-yl)-5-bromo-2,6-dimethylpyridin-3-yl)-2-(tert-butoxy)acetate (0.860 g, 1.729 mmol, 40.4% yield) as colorless viscous oil (came out with 10-20% EtOAc), LCMS (M+H)=499.3 and recovered (S)-ethyl 2-(4-(4-(allyloxy)-4-methylpiperidin-1-yl)-5-bromo-2,6-dimethylpyridin-3-yl)-2-hydroxyacetate (0.9565 g, 2.167 mmol, 50.6% yield).

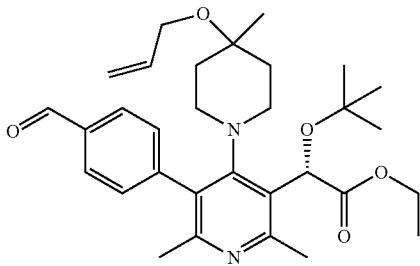 [SMILES: C=CCOC1(C)CCN(c2c(-c3ccc(C=O)cc3)c(C)nc(C)c2[C@H](OC(C)(C)C)C(=O)OCC)CC1]

(S)-Ethyl 2-(4-(4-(allyloxy)-4-methylpiperidin-1-yl)-5-(4-formylphenyl)-2,6-dimethylpyridin-3-yl)-2-(tert-butoxy)acetate A mixture of (S)-ethyl 2-(4-(4-(allyloxy)-4-methylpiperidin-1-yl)-5-bromo-2,6-dimethylpyridin-3-yl)-2-(tert-butoxy)acetate (0.261 g, 0.525 mmol), (4-formylphenyl)boronic acid (0.157 g, 1.049 mmol) and 2M Na$_2$CO$_3$ (0.656 ml, 1.312 mmol) in DMF (6 mL) was degassed for 10 min. Then, Pd(Ph$_3$P)$_4$ (0.030 g, 0.026 mmol) was added, degassed for 5 min and placed in a pre-heated oil bath at 90° C. After 7 h at 95° C., cooled, diluted with ether (50 mL), washed with water (4×10 mL), brine (10 mL), dried (MgSO$_4$), filtered, concentrated and the residue purified by flash chromatography using 20-50% EtOAc/Hex to afford (S)-ethyl 2-(4-(4-(allyloxy)-4-methylpiperidin-1-yl)-5-(4-formylphenyl)-2,6-dimethylpyridin-3-yl)-2-(tert-butoxy)acetate (0.2457 g, 0.470 mmol, 90% yield) as pale yellow paste. LCMS (M+H)=523.4.

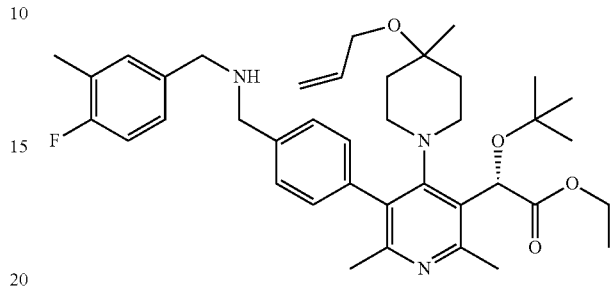

(S)-Ethyl 2-(4-(4-(allyloxy)-4-methylpiperidin-1-yl)-5-(4-(((4-fluoro-3-methylbenzyl)amino)methyl)phenyl)-2,6-dimethylpyridin-3-yl)-2-(tert-butoxy)acetate To a stirred solution of (S)-ethyl 2-(4-(4-(allyloxy)-4-methylpiperidin-1-yl)-5-(4-formylphenyl)-2,6-dimethylpyridin-3-yl)-2-(tert-butoxy)acetate (0.245 g, 0.469 mmol) and (4-fluoro-3-methylphenyl)methanamine (0.065 g, 0.469 mmol) was added NaCNBH$_4$ (0.039 g, 0.623 mmol) and ZnCl$_2$ (0.032 g, 0.234 mmol) and stirred for 6 h at rt. Then, diluted with EtOAc (50 mL), washed with sat. Na$_2$CO$_3$ (10 mL), brine (10 mL), dried (MgSO$_4$), filtered, concentrated and purified by flash chromatography using 50, 70 and 80% EtOAc/Hex to provide (S)-ethyl 2-(4-(4-(allyloxy)-4-methylpiperidin-1-yl)-5-(4-(((4-fluoro-3-methylbenzyl)amino)methyl)phenyl)-2,6-dimethylpyridin-3-yl)-2-(tert-butoxy)acetate (0.237 g, 0.367 mmol, 78% yield) as pale yellow paste. $^1$H NMR (500 MHz, CDCl) δ 7.37-7.46 (m, 2H), 7.20-7.27 (m, 2H), 7.09-7.19 (m, 2H), 6.96-7.02 (m, 1H), 6.02 (br. s., 1H), 5.84-5.95 (m, 0.3H), 5.63-5.74 (m, 0.7H), 5.26 (d, J=17.2 Hz, 0.3H), 5.06-5.15 (m, 1H), 5.00 (d, J=10.3 Hz, 0.7H), 4.27 (qd, J=7.1, 10.8 Hz, 1H), 4.12-4.21 (m, 1H), 3.90 (br. s., 0.6H), 3.87 (s, 1.4H), 3.81 (s, 1.4H), 3.78 (br. s., 0.6H), 3.69 (dd, J=5.2, 12.1 Hz, 0.7H), 3.57 (dd, J=5.0, 12.2 Hz, 0.7H), 3.39 (d, J=11.7 Hz, 0.3H), 3.16 (d, J=11.7 Hz, 0.7H), 3.01-3.08 (m, 0.7H), 2.80 (t, J=11.7 Hz, 0.3H), 2.63 (s, 3H), 2.47-2.56 (m, 0.3H), 2.30 (d, J=1.9 Hz, 3H), 2.19 (s, 3H), 2.15-2.23 (m, 1.3H), 1.99 (t, J=11.3 Hz, 0.3H), 1.64-1.72 (m, 1.4H), 1.54-1.61 (m, 2H), 1.41 (dt, J=4.8, 12.9 Hz, 0.7H), 1.26 (t, J=6.9 Hz, 3H), 1.21 (s, 9H), 1.12 (s, 2H), 0.90 (s, 1H). LCMS (M+H)=646.5.

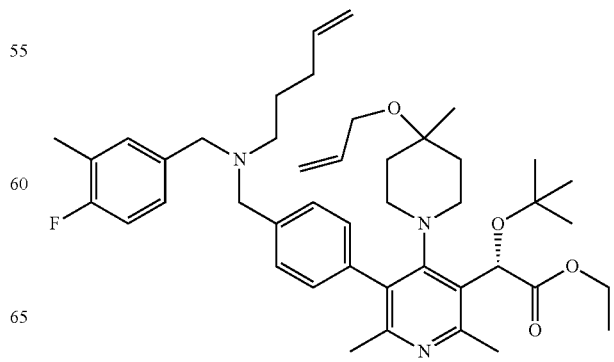

(S)-Ethyl 2-(4-(4-(allyloxy)-4-methylpiperidin-1-yl)-5-(4-(((4-fluoro-3-methylbenzyl)(pent-4-en-1-yl)amino)methyl)phenyl)-2,6-dimethylpyridin-3-yl)-2-(tert-butoxy)acetate To a stirred solution of (S)-ethyl 2-(4-(4-(allyloxy)-4-methylpiperidin-1-yl)-5-(4-(((4-fluoro-3-methylbenzyl)amino)methyl)phenyl)-2,6-dimethylpyridin-3-yl)-2-(tert-butoxy)acetate (0.074 g, 0.115 mmol) and pent-4-enal (0.019 g, 0.229 mmol) in MeOH (3 mL) was added at once NaCNBH₄ (10.80 mg, 0.172 mmol) and ZnCl₂ (0.012 g, 0.086 mmol) at rt. After 3 h, the reaction mixture was diluted with ether (50 mL), washed with sat. Na₂CO₃ (5 mL), water (5 mL), brine (5 mL), dried (MgSO4), filtered and concentrated to give (S)-ethyl 2-(4-(4-(allyloxy)-4-methylpiperidin-1-yl)-5-(4-(((4-fluoro-3-methylbenzyl)(pent-4-en-1-yl)amino)methyl)phenyl)-2,6-dimethylpyridin-3-yl)-2-(tert-butoxy)acetate which was used in the next step without purification. $^1$H NMR (500 MHz, CDCl$_3$) δ 7.33-7.43 (m, 2H), 7.14-7.21 (m, 3H), 7.09 (d, J=7.7 Hz, 1H), 6.93-6.98 (m, 1H), 6.02 (br. s., 1H), 5.71-5.90 (m, 2H), 5.58-5.68 (m, 0.7H), 5.21-5.27 (m, 0.3H), 5.02-5.14 (m, 2H), 4.87-5.00 (m, 3H), 4.26 (qd, J=7.1, 10.7 Hz, 1H), 4.16 (qd, J=7.1, 10.7 Hz, 1H), 3.81-3.87 (m, 0.7H), 3.56-3.68 (m, 3H), 3.43-3.55 (m, 3H), 3.37 (d, J=10.4 Hz, 0.3H), 3.15 (d, J=10.9 Hz, 0.7H), 3.04 (t, J=11.4 Hz, 0.7H), 2.76-2.83 (m, 0.3H), 2.62 (s, 3H), 2.41-2.53 (m, 3H), 2.29 (d, J=1.3 Hz, 3H), 2.18 (s, 3H), 2.03-2.09 (m, 2H), 1.50-1.70 (m, 4H), 1.25 (t, J=7.0 Hz, 3H), 1.21 (s, 9H), 1.10 (s, 2H), 0.78 (br. s., 1H). LCMS (M+H)=714.4.

EXAMPLE 1

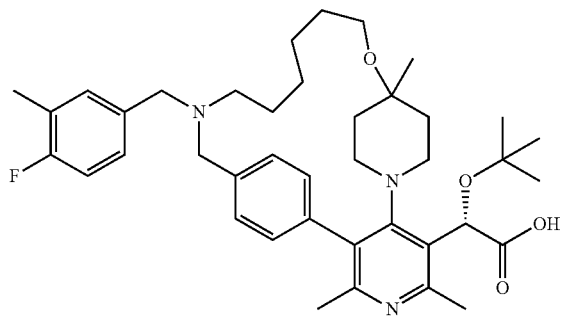 [SMILES: Cc1cc(CN2CCCCCCOC3(C)CCN(CC3)c3c(c(C)nc(C)c3[C@H](OC(C)(C)C)C(=O)O)-c3ccc(cc3)C2)ccc1F]

(2S)-2-(tert-Butoxy)-2-{13-[(4-fluoro-3-methylphenyl)methyl]-4,6,21-trimethyl-20-oxa-1,5,13-triazatetracyclo[19.2.2.2$^{8,11}$.0$^{2,7}$]heptacosa-2,4,6,8,10,26-hexaen-3-yl}acetic acid To a stirred solution of (S)-ethyl 2-(4-(4-(allyloxy)-4-methylpiperidin-1-yl)-5-(4-(((4-fluoro-3-methylbenzyl)(pent-4-en-1-yl)amino)methyl)phenyl)-2,6-dimethylpyridin-3-yl)-2-(tert-butoxy)acetate (0.082 g, 0.115 mmol) and Ts-OH.H2O (0.044 g, 0.230 mmol) in 1,2-dichloroethane was added Hoveyda-Grubbs catalyst 2nd generation (7.21 mg, 0.012 mmol) and heated to 70° C. over 25 min. After 50 min at 70° C., the reaction mixture was cooled and concentrated to about 5 mL. To this solution was added MeOH (5 mL) and NaBH₄ (0.013 g, 0.345 mmol) at rt. Note: Lots of gas evolved as soon as NaBH4 was added. After 30 min added additional NaBH₄ (0.013 g, 0.345 mmol). LCMS after 2.5 h showed 1:1 mixture of sm and desired product. So, added additional NaBH₄ (0.013 g, 0.345 mmol) and stirred overnight (18 h). LCMS at this point showed completion of reaction. The reaction mixture was diluted with EtOAc (50 mL), washed with water (3×10 mL), brine (5 mL), dried (MgSO₄), filtered and concentrated to give crude saturated ester as brown residue (0.085 mg) which was used in the next step without purification. LCMS (M+H)=688.3.

A mixture of above crude ester and LiOH (0.028 g, 1.150 mmol) in 9:1 EtOH/H₂O (3 mL) was refluxed for 4 h. Then, cooled and purified by prep-HPLC to afford desired macrocyclic caboxylic acid (0.0447 g, 0.068 mmol, 58.9% yield) as off-white solid. $^1$H NMR (500 MHz, CDCl$_3$) δ 7.59 (d, J=7.7 Hz, 1H), 7.25-7.28 (m, 2H), 7.23 (d, J=7.6 Hz, 1H), 7.13 (dd, J=1.6, 7.9 Hz, 1H), 6.96-7.03 (m, 2H), 5.90 (br. s., 1H), 3.97 (d, J=13.4 Hz, 1H), 3.77 (d, J=14.0 Hz, 1H), 3.69 (br. s., 1H), 3.24-3.35 (m, 2H), 3.10-3.20 (m, 2H), 2.96 (t, J=12.0 Hz, 1H), 2.70-2.77 (m, 1H), 2.69 (s, 3H), 2.31 (d, J=1.3 Hz, 3H), 2.27-2.36 (m, 2H), 2.16-2.24 (m, 1H), 2.12 (s, 3H), 1.67-1.84 (m, 3H), 1.54-1.64 (m, 3H), 1.44-1.53 (m, 1H), 1.35-1.42 (m, 2H), 1.26-1.34 (m, 3H), 1.24 (s, 9H), 1.10 (s, 3H). LCMS (M+H)=660.3.

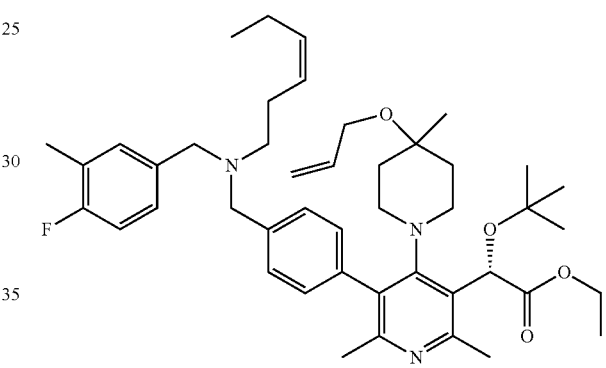

(S,Z)-Ethyl 2-(4-(4-(allyloxy)-4-methylpiperidin-1-yl)-5-(4-(((4-fluoro-3-methylbenzyl)(hex-3-en-1-yl)amino)methyl)phenyl)-2,6-dimethylpyridin-3-yl)-2-(tert-butoxy)acetate To a stirred solution of (S)-ethyl 2-(4-(4-(allyloxy)-4-methylpiperidin-1-yl)-5-(4-(((4-fluoro-3-methylbenzyl)amino)methyl)phenyl)-2,6-dimethylpyridin-3-yl)-2-(tert-butoxy)acetate (0.082 g, 0.127 mmol) and 50 wt % (Z)-hex-3-enal/triacetin (0.050 g, 0.254 mmol) in MeOH (3 mL) was added at once NaCNBH₄ (0.012 g, 0.190 mmol) and ZnCl₂ (0.013 g, 0.095 mmol) at rt. After 3 h, LCMS showed incomplete reaction. So, added additional 50 wt % (Z)-hex-3-enal/triacetin (0.050 g, 0.254 mmol) and NaCNBH₄ (0.012 g, 0.190 mmol) and continued stirring at rt for 1.5 h. Then, the reaction mixture was diluted with ether (50 mL), washed with sat. Na₂CO₃ (5 mL), water (5 mL), brine (5 mL), dried (MgSO₄), filtered and concentrated to give (S,Z)-ethyl 2-(4-(4-(allyloxy)-4-methylpiperidin-1-yl)-5-(4-(((4-fluoro-3-methylbenzyl)(hex-3-en-1-yl)amino)methyl)phenyl)-2,6-dimethylpyridin-3-yl)-2-(tert-butoxy)acetate as which was purified by pre-HPLC (first run nothing cameout, so in the second run allowed to run for additional 15 min at 100% solvent B) to afford mixture of compounds (0.0 mg) which was used in the next step without further purification. LCMS (M+H)=728.5.

EXAMPLE 2

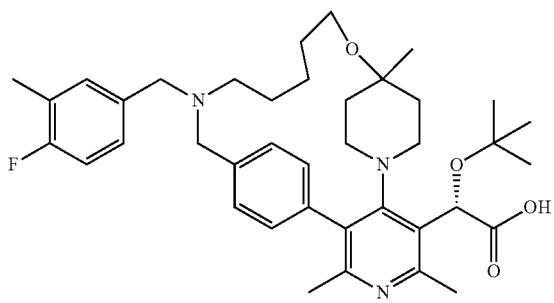 [SMILES: Cc1cc(CN2CCCCCOC3(C)CCN(CC3)c3c(c(C)nc(C)c3[C@H](OC(C)(C)C)C(=O)O)-c3ccc(cc3)C2)ccc1F]

(2S)-2-(tert-Butoxy)-2-{13-[(4-fluoro-3-methylphenyl)methyl]-4,6,20-trimethyl-19-oxa-1,5,13-triazatetracyclo[18.2.2.2$^{8,11}$.0$^{2,7}$]hexacosa-2,4,6,8,10,25-hexaen-3-yl}acetic acid To a stirred solution of (S,Z)-ethyl 2-(4-(4-(allyloxy)-4-methylpiperidin-1-yl)-5-(4-(((4-fluoro-3-methylbenzyl)(hex-3-en-1-yl)amino)methyl)phenyl)-2,6-dimethylpyridin-3-yl)-2-(tert-butoxy)acetate (0.063 g, 0.087 mmol) and Ts-OH.H$_2$O (0.033 g, 0.173 mmol) in 1,2-dichloroethane (20 mL) was added Hoveyda-Grubbs catalyst 2nd generation (5.42 mg, 8.65 μmol) and warmed to 75° C. over 25 min. After 80 min at 75° C., the reaction mixture was concentrated about 1 mL. LCMS (M+H)=672.4.

To this mixture was added MeOH (5 mL) and NaBH$_4$ (0.016 g, 0.433 mmol) at rt. LCMS after 17 h showed presence of about 40% unreduced olefine. So, added additional NaBH4 (0.016 g, 0.433 mmol) and continued stirring at rt for 24 h. Then, concentrated and the dark brown residue was taken up in EtOAc (50 mL), washed with water (2×10 mL), brine (10 mL), dried (MgSO$_4$), filtered and concentrated to give ester as which was used in the next step without purification. LCMS (M+H)=674.4.

A mixture of above crude ester and LiOH (0.021 g, 0.865 mmol) in 9:1 EtOH/H$_2$O (2 mL) was refluxed for 5 h. Then, cooled and purified by prep-HPLC to afford desired macrocyclic carboxylic acid, 2 TFA (0.013 g, 0.015 mmol, 17.19% yield) as white solid. $^1$H NMR (500 MHz, CDCl$_3$) δ 7.91 (br. s., 1H), 7.44 (d, J=6.8 Hz, 1H), 7.33-7.42 (m, 3H), 7.13 (t, J=8.8 Hz, 1H), 7.06 (br.s., 1H), 5.71 (br. s., 1H), 4.66 (br. s., 1H), 4.32-4.52 (m, 2H), 3.74 (br. s., 1H), 3.59 (br. s., 1H), 3.30 (br. s., 1H), 2.98-3.17 (m, 3H), 2.80 (s, 3H), 2.74-2.84 (br. s., 1H), 2.35 (s, 6H), 2.30 (d, J=11.2 Hz, 1H), 1.93 (br. s., 1H), 1.62-1.85 (m, 5H), 1.47-1.55 (m, 1H), 1.39-1.45 (m, 1H), 1.29-1.37 (m, 3H), 1.23 (s, 9H), 1.13 (s, 3H). LCMS (M+H)=646.3.

(S)-Ethyl 2-(4-(4-(allyloxy)-4-methylpiperidin-1-yl)-5-(4-((tert-butyldimethylsilyl)oxy)phenyl)-2,6-dimethylpyridin-3-yl)-2-(tert-butoxy)acetate A mixture of (S)-ethyl 2-(4-(4-(allyloxy)-4-methylpiperidin-1-yl)-5-bromo-2,6-dimethylpyridin-3-yl)-2-(tert-butoxy)acetate (0.99 g, 1.990 mmol), (4-((tert-butyldimethylsilyl)oxy)phenyl)boronic acid (1.004 g, 3.98 mmol) and 2M Na$_2$CO$_3$ (2.488 ml, 4.98 mmol) in DMF (20 mL) was degassed for 10 min. Then, Pd(Ph$_3$P)$_4$ (0.115 g, 0.100 mmol) was added, degassed for 5 min and placed in a pre-heated oil bath at 90° C. After 8 h, the reaction mixture was diluted with ether (100 mL), washed with water (4×25 mL) and brine (10 mL). The combined aq layers extracted with ether (75 mL) and combined ether layers dried (MgSO$_4$), filtered, concentrated and the brown residue was purified by flash chromatography using 20, 30 and 40% EtOAc/Hex to afford (S)-ethyl 2-(4-(4-(allyloxy)-4-methylpiperidin-1-yl)-5-(4-((tert-butyldimethylsilyl)oxy)phenyl)-2,6-dimethylpyridin-3-yl)-2-(tert-butoxy)acetate as white solid. LCMS (M+H)=511.3.

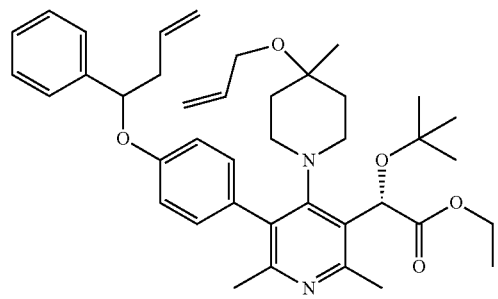

(2S)-Ethyl 2-(4-(4-(allyloxy)-4-methylpiperidin-1-yl)-2,6-dimethyl-5-(4-((1-phenylbut-3-en-1-yl)oxy)phenyl)pyridin-3-yl)-2-(tert-butoxy)acetate To a stirred solution of (S)-ethyl 2-(4-(4-(allyloxy)-4-methylpiperidin-1-yl)-5-(4-hydroxyphenyl)-2,6-dimethylpyridin-3-yl)-2-(tert-butoxy)acetate (0.04 g, 0.078 mmol), 1-phenylbut-3-en-1-ol (0.058 g, 0.392 mmol) and Ph$_3$P (0.062 g, 0.235 mmol) in THF (3 mL) was added DEAD (0.037 ml, 0.235 mmol) at 0° C. After 1 h, cold bath was removed and stirred at rt for 15 h. Then, concentrated and purified by prep-HPLC to afford (2S)-ethyl 2-(4-(4-(allyloxy)-4-methylpiperidin-1-yl)-2,6-dimethyl-5-(4-((1-phenylbut-3-en-1-yl)oxy)phenyl)pyridin-3-yl)-2-(tert-butoxy)acetate (0.03986 g, 0.062 mmol, 79% yield) as colorless paste. LCMS (M+H)=641.4.

EXAMPLES 3 AND 4

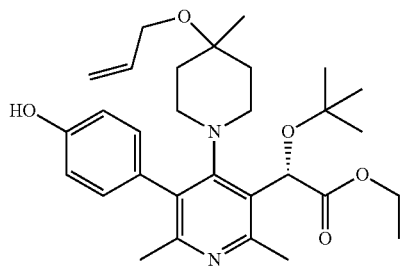 [SMILES: C=CCOC1(C)CCN(c2c(-c3ccc(O)cc3)c(C)nc(C)c2[C@H](OC(C)(C)C)C(=O)OCC)CC1]

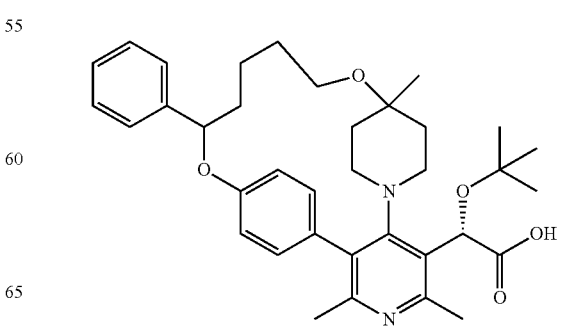

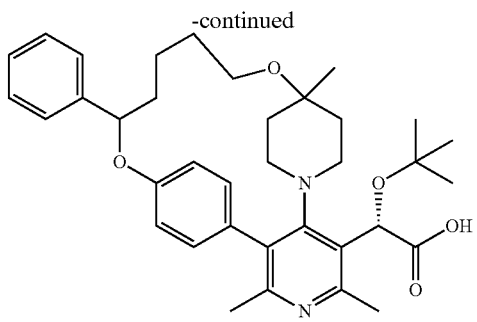

(2S)-2-(tert-Butoxy)-2-{4,6,19-trimethyl-13-phenyl-12,18-dioxa-1,5-diazatetracyclo[17.2.2.2$^{8,11}$.0$^{2,7}$]pentacosa-2,4,6,8,10,24-hexaen-3-yl}acetic acid To a stirred solution of (2S)-ethyl 2-(4-(4-(allyloxy)-4-methylpiperidin-1-yl)-2,6-dimethyl-5-(4-((1-phenylbut-3-en-1-yl)oxy)phenyl)pyridin-3-yl)-2-(tert-butoxy)acetate (0.0385 g, 0.060 mmol) and Ts-OH.H$_2$O (0.011 g, 0.060 mmol) in 1,2-dichloroethane was added Hoveyda-Grubbs catalyst 2nd generation (3.76 mg, 6.01 μmol) and warmed to 70° C. over 15 min. After 60 min, the reaction mixture was cooled to rt.

To the above mixture was added EtOH (1 mL) and NaBH$_4$ (6.82 mg, 0.180 mmol), stirred for 21 h. The reaction mixture was diluted with EtOAc (25 mL), washed with water (2×10 mL), brine (5 mL), dried (MgSO$_4$), filtered and concentrated to give crude ester as brown paste which was used in the next step without purification.

A mixture of above residue and LiOH (0.014 g, 0.601 mmol) in 9:1 EtOH/H$_2$O (2 mL) was refluxed for 4 h. Then, cooled and purified by prep-HPLC to afford as a mixture of diastereomers (0.0247 g, 70%). This mixture was repurified by using another prep using different buffer to afford individual diastereomers. Diastereomer 1: (0.011 g, 0.019 mmol, 31.2% yield) as white solid. $^1$H NMR (500 MHz, CDCl$_3$) δ 7.54-7.57 (m, 2H), 7.41-7.46 (m, 2H), 7.33-7.37 (m, 1H), 7.22-7.26 (m, 3H), 7.05-7.08 (m, 1H), 5.92 (br. s., 1H), 5.49 (d, J=6.9 Hz, 1H), 3.21-3.30 (m, 2H), 3.00-3.09 (m, 2H), 2.68 (s, 3H), 2.45 (t, J=11.0 Hz, 1H), 2.33 (d, J=11.4 Hz, 1H), 2.24 (s, 3H), 1.90-2.04 (m, 2H), 1.61-1.73 (m, 4H), 1.42-1.55 (m, 4H), 1.29 (s, 9H), 1.11 (s, 3H). LCMS (M+H)=587.4.

Diastereomer 2: (0.0115 g, 0.020 mmol, 32.6% yield) as white solid. $^1$H NMR (500 MHz, CDCl$_3$) δ 7.53-7.56 (m, 2H), 7.41-7.45 (m, 2H), 7.33-7.37 (m, 1H), 7.27-7.30 (m, 1H), 7.20-7.23 (m, 1H), 7.14-7.17 (m, 1H), 7.05-7.09 (m, 1H), 5.95 (br. s., 1H), 5.67 (dd, J=3.3, 9.6 Hz, 1H), 3.33 (d, J=10.6 Hz, 1H), 3.23 (td, J=5.4, 7.9 Hz, 1H), 3.04 (t, J=10.9 Hz, 1H), 2.96 (td, J=5.7, 7.8 Hz, 1H), 2.67 (s, 3H), 2.27-2.38 (m, 2H), 2.26 (s, 3H), 2.04-2.14 (m, 1H), 1.83-1.92 (m, 1H), 1.59-1.71 (m, 3H), 1.37-1.56 (m, 5H), 1.29 (s, 9H), 1.10 (s, 3H). LCMS (M+H)=587.4.

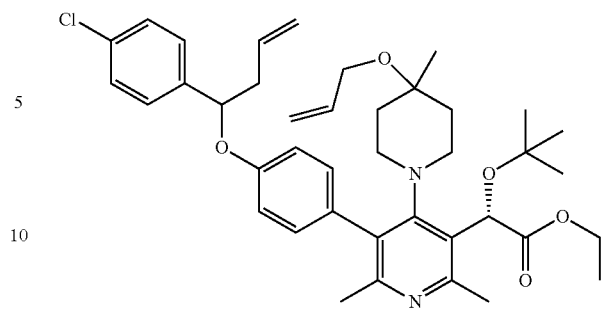

(2S)-Ethyl 2-(4-(4-(allyloxy)-4-methylpiperidin-1-yl)-5-(4-(((1-(4-chlorophenyl)but-3-en-1-yl)oxy)phenyl)-2,6-dimethylpyridin-3-yl)-2-(tert-butoxy)acetate To a stirred solution of (S)-ethyl 2-(4-(4-(allyloxy)-4-methylpiperidin-1-yl)-5-(4-hydroxyphenyl)-2,6-dimethylpyridin-3-yl)-2-(tert-butoxy)acetate (0.08 g, 0.157 mmol), 1-(4-chlorophenyl)but-3-en-1-ol (0.143 g, 0.783 mmol) and Ph$_3$P (0.123 g, 0.470 mmol) in THF (5 mL) was added dropwise DEAD (0.074 ml, 0.470 mmol) at 0° C. After 1 h, cold bath was removed and stirred for 18 h at rt. Then, concentrated and purified by prep-HPLC to afford (2S)-ethyl 2-(4-(4-(allyloxy)-4-methylpiperidin-1-yl)-5-(4-((1-(4-chlorophenyl)but-3-en-1-yl)oxy)phenyl)-2,6-dimethylpyridin-3-yl)-2-(tert-butoxy)acetate (0.0847 g, 0.125 mmol, 80% yield) as colorless paste. LCMS (M+H)=675.3.

EXAMPLES 5 AND 6

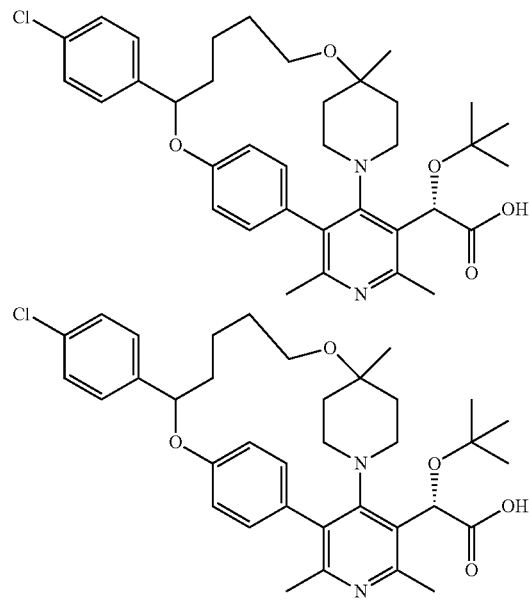

(2S)-2-(tert-Butoxy)-2-[13-(4-chlorophenyl)-4,6,19-trimethyl-12,18-dioxa-1,5-diazatetracyclo[17.2.2.2$^{8,11}$.0$^{2,7}$]pentacosa-2,4,6,8,10,24-hexaen-3-yl]acetic acid To a solution of (2S)-ethyl 2-(4-(4-(allyloxy)-4-methylpiperidin-1-yl)-5-(4-((1-(4-chlorophenyl)but-3-en-1-yl)oxy)

phenyl)-2,6-dimethylpyridin-3-yl)-2-(tert-butoxy)acetate (0.0845 g, 0.125 mmol) and Ts-OH.H$_2$O (0.024 g, 0.125 mmol) in 1,2-dichloroethane (20 mL) was added Hoveyda-Grubbs catalyst 2nd generation (7.84 mg, 0.013 mmol) at rt. The resulting mixture was warmed to 70° C. over 30 min. After min, the reaction mixture was concentrated ~10 mL and used in the next step. LCMS (M+H)=647.5.

To the above crude reaction mixture was added EtOH (1 mL) and NaBH$_4$ (0.014 g, 0.375 mmol) and stirred for 15 h at rt. LCMS at this point showed incomplete reaction. So, added additional NaBH$_4$ (0.014 g, 0.375 mmol) and stirred for 8 h at rt. Then, the reaction mixture was diluted with EtOAc (25 mL), washed with water (2×10 mL), brine (5 mL), dried (MgSO$_4$), filtered and concentrated to give crude ester as brown solid which was used in the next step without purification. LCMS (M+H)=647.5.

A mixture of above solid and LiOH (0.030 g, 1.251 mmol) in 9:1 EtOH/H$_2$O (2 mL) was refluxed for 4 h. Then, cooled and purified to afford two compounds. Diastereomer 1 (0.02 g, 0.032 mmol, 25.7% yield) as white solid. $^1$H NMR (500 MHz, CDCl$_3$) δ 7.46-7.50 (m, 2H), 7.38-7.42 (m, 2H), 7.25-7.28 (m, 1H), 7.21-7.24 (m, 2H), 7.05-7.09 (m, 1H), 5.91 (br. s., 1H), 5.46 (dd, J=2.6, 7.8 Hz, 1H), 3.19-3.29 (m, 2H), 3.00-3.07 (m, 2H), 2.68 (s, 3H), 2.39-2.48 (m, 1H), 2.32 (d, J=11.2 Hz, 1H), 2.24 (s, 3H), 1.86-1.98 (m, 2H), 1.59-1.72 (m, 4H), 1.39-1.54 (m, 4H), 1.29 (s, 9H), 1.10 (s, 3H). LCMS (M+H)=621.4.

Diastereomer 2 (0.026 g, 0.042 mmol, 33.4% yield) as white solid. $^1$H NMR (500 MHz, CDCl$_3$) δ 7.46-7.50 (m, 2H), 7.38-7.42 (m, 2H), 7.25 (dd, J=2.6, 8.6 Hz, 1H), 7.22 (dd, J=2.2, 8.4 Hz, 1H), 7.13-7.16 (m, 1H), 7.07 (dd, J=2.2, 8.3 Hz, 1H), 5.99 (br. s., 1H), 5.64 (dd, J=3.2, 9.5 Hz, 1H), 3.30 (d, J=10.3 Hz, 1H), 3.22 (td, J=5.4, 7.9 Hz, 1H), 3.02 (t, J=11.2 Hz, 1H), 2.93-2.99 (m, 1H), 2.67 (s, 3H), 2.26 (s, 3H), 2.21-2.38 (m, 2H), 2.00-2.09 (m, 1H), 1.79-1.88 (m, 1H), 1.34-1.63 (m, 8H), 1.29 (s, 9H), 1.10 (s, 3H). LCMS (M+H)=621.4.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed:

1. A compound of Formula I

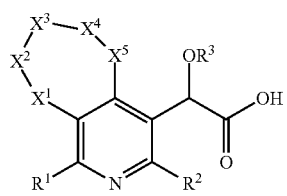

where:
R$^1$ is alkyl;
R$^2$ is alkyl;
R$^3$ is alkyl or haloalkyl;
R$^4$ is (Ar$^1$)alkyl or Ar$^1$;
Ar$^1$ is phenyl substituted with 0-3 substituents selected from halo, alkyl, haloalkyl, alkoxy, and haloalkoxy;
X$^1$ is phenyl;
X$^2$ is absent, O, NR$^4$, or CH$_2$NR$^4$;
X$^3$ is alkylene or alkenylene where the alkylene or alkenylene can be substituted with 0-1 Ar$^1$ substituents;
X$^4$ is absent or O; and
X$^5$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, and haloalkoxy;
or a pharmaceutically acceptable salt thereof.

2. A compound of claim 1 where R$^3$ is alkyl; R$^4$ is (Ar$^1$)alkyl or Ar$^1$; Ar$^1$ is phenyl substituted with 0-3 substituents selected from halo, alkyl, haloalkyl, alkoxy, and haloalkoxy; X$^2$ is absent or CH$_2$NR$^4$; X$^3$ is alkylene or alkenylene where the alkylene or alkeneyle can be substituted with 0-1 Ar$^1$ substituents; X$^4$ is O; and X$^5$ is piperidinyl substituted with 0-3 alkyl substituents; or a pharmaceutically acceptable salt thereof.

3. A compound of claim 1 where X$^2$ is CH$_2$NR$^4$; X$^3$ is alkylene; and X$^4$ is O.

4. A compound of claim 1 where X$^2$ is O; X$^3$ is alkylene or alkenylene substituted with 1 Ar$^1$ substituents; and X$^4$ is O.

5. A compound of claim 1 where X$^5$ is piperidinyl substituted with 0-3 substituents selected from halo, alkyl, haloalkyl, alkoxy, and haloalkoxy.

6. A compound of claim 1 selected from the group consisting of
(2S)-2-(tert-Butoxy)-2-{13-[(4-fluoro-3-methylphenyl)methyl]-4,6,21-trimethyl-20-oxa-1,5,13-triazatetracyclo[19.2.2.2$^{8,11}$.0$^{2,7}$]heptacosa-2,4,6,8,10,26-hexaen-3-yl}acetic acid;
(2S)-2-(tert-Butoxy)-2-{13-[(4-fluoro-3-methylphenyl)methyl]-4,6,20-trimethyl-19-oxa-1,5,13-triazatetracyclo[18.2.2.2$^{8,11}$.0$^{2,7}$]hexacosa-2,4,6,8,10,25-hexaen-3-yl}acetic acid;
(2S)-2-(tert-Butoxy)-2-{4,6,19-trimethyl-13-phenyl-12,18-dioxa-1,5-diazatetracyclo[17.2.2.2$^{8,11}$.0$^{2,7}$]pentacosa-2,4,6,8,10,24-hexaen-3-yl}acetic acid; and
(2S)-2-(tert-Butoxy)-2-[13-(4-chlorophenyl)-4,6,19-trimethyl-12,18-dioxa-1,5-diazatetracyclo[17.2.2.2$^{8,11}$.0$^{2,7}$]pentacosa-2,4,6,8,10,24-hexaen-3-yl]acetic acid;
or a pharmaceutically acceptable salt thereof.

7. A composition useful for treating HIV infection comprising a therapeutic amount of a compound of claim 1 and a pharmaceutically acceptable carrier.

8. A method for treating HIV infection comprising administering a therapeutically effective amount of a compound of claim 1, or a pharmaceutically acceptable salt thereof, to a patient in need thereof.

* * * * *